United States Patent [19]

Parsons

[11] Patent Number: 5,180,715
[45] Date of Patent: Jan. 19, 1993

[54] IRRIGATION OF INTERNAL BLADDER SURFACES IN MAMMALS WITH SODIUM PENTOSANPOLYSULFATE

[75] Inventor: C. Lowell Parsons, San Diego

[73] Assignee: The Regents of the University of California, Oakland, Calif.

[21] Appl. No.: 387,402

[22] Filed: Jul. 31, 1989

Related U.S. Application Data

[63] Continuation of Ser. No. 416,638, Sep. 10, 1982, abandoned, which is a continuation-in-part of Ser. No. 207,206, Nov. 17, 1980, abandoned.

[51] Int. Cl.$^5$ .............................................. A61K 31/70
[52] U.S. Cl. ........................................ 514/54; 514/23
[58] Field of Search ............................. 514/54, 56, 23

[56] References Cited

PUBLICATIONS

Walb et al., Chemical Abstracts, vol. 75 (1971) No. 33179s "In vitro studies on the mode and differences of heparin action".
Johnson et al, Cancer Treatment Reviews vol. 2 (1975) pp. 1-5, "The clinical impact of screening and other experimental tumor studies".
Hanno et al, Chemical Abstracts vol. 90 (1979) No. 48542p "The protective effect of heparin in experimental bladder infections".
Parsons et al, Chemical Abstracts, vol. 93 (1980) No. 24207u, "Antibacterial activity of bladder surface mucin dupl. in the rabbit bladder . . . ".

Primary Examiner—Ronald W. Griffin
Assistant Examiner—Elli Peselev
Attorney, Agent, or Firm—Morrison & Foerster

[57] ABSTRACT

The method of treating bladder infections, interstitial cystitis and tumors in mammals which comprises the irrigation of the internal bladder and associated surfaces with an irrigating solution containing an effective amount of sodium pentosanpolysulfate. Also, the treatment of interstitial cystitis by the oral administration of sodium pentosanpolysulfate at high dosages on the order of 200 mg. per day or more.

11 Claims, No Drawings

IRRIGATION OF INTERNAL BLADDER SURFACES IN MAMMALS WITH SODIUM PENTOSANPOLYSULFATE

This application is a continuation of application Ser. No. 06/416,638, filed Sep. 10, 1982, abandoned, which is a continuation-in-part of Ser. No. 207,206, filed Nov. 17, 1980, now abandoned.

BACKGROUND OF THE INVENTION

It has long been known that the urinary bladder in the normal state is remarkably resistant to infection, although little has been described concerning any intrinsic antibacterial defense mechanism. A vesical mucosal bactericidal activity has been suggested, Cobbs, G. C. and D. Kaye (1967)., "Antibacterial mechanisms in the urinary bladder", Yale J. Biol. Med. 40:93-108; Cox, C. E., and F. Hinman, Jr. (1961), "Experiments with induced bacteriuria, vesical emptying and bacterial growth on the mechanism of bladder defense to infection", J. Urol. 86:739-748;and Norden, C. W., G. M. Green, and E. H. Kass, (1968), "Antibacterial mechanisms of the urinary bladder", J. Clin. Invest. 47:2689-2700, but its existence has not been corroborated by other investigators, Mulholland, S. G., E. A. Foster, A. J. Paquin, Jr., and J. Y. Gillenwater (1969), "The effect of rabbit vesical mucosa on bacterial growth", Invest. Urol. 6:593-604. It seemed unlikely that chance alone accounted for the bladder's ability to maintain a sterile lumen in the face of direct contact with environmental organisms; rather, antibacterial defense mechanisms might actively maintain this equilibrium. In this regard, I became interested in the concept of bacterial virulence depending on the ability of bacteria to adhere to a mucous surface.

Adherence has been postulated to play a role in bacterial virulence at many mucous surfaces including the gastrointestinal tract, the genitourinary tract, and the oral cavity, Ellen, R. P. and R. J. Gibbons (1972),"M protein-associated adherence of *Streptococcus pyogenes* to epithelial surfaces: prerequisite for virulence", Infect. Immuno. 5:826-830; Gibbons, R. J., and J. van Houte (1971), "Selective bacterial adherence to oral epithelial surfaces and its role as an ecological determinant", Infect. Immun. 3:567-573; Punsalong, A. P., Jr., and W. D. Sawyer (1973), "Role of pili in the virulence of *Neisseria gonorrhoeae*," Infect. Immun. 8:255-263; Sobelavsky. O., B. Prescott, and R. M. Chanock (1968), "Adsorption of *Mycoplasma pneumoniae* to neuraminic acid receptors of various cells and possible role in virulence", J. Bacteriol. 96:695-705; Svanborg-Eden, C., B. Eriksson, and L. A. Hanson (1977), "Adhesion of *Escherichia coli* to human uroepithelial cells in vitro", Infect. Immun. 18:767-774; Swanson, Jr. (1973), "Studies on gonococcus infection. IV. Pili: their role in attachment of gonococci to tissue culture cells", J. Exp. Med. 137:571-589; Swanson, Jr., G. King, and B. Zeligs (1975), "Studies on gonococcus infection. VIII. $^{125}$Iodine labeling of gonococci and studies on their in vitro interactions with eukaryotic cells", Infect. Immun. 11:453-459; Ward, M. E., and P. J. Watt (1972), "Adherence of *Neisseria gonorrhoeae* to urethral mucosal cells: an electron-microscopic study of human gonorrhea", J. Infect. Dis. 126:601-605; and Ward, M. E., P. J. Watt, and J. N. Robertson (1974), "The human fallopian tube: a laboratory model for gonococcal infection", J. Infect. Dis. 129:650-659.

The main theme of data obtained in these systems is that microbial ability to infect a surface is directly proportional to its ability to adhere to the mucosal cells. If adherence is important to bacterial virulence, it is possible that the body produces antiadherence factors as a counter measure. In the urinary bladder, an antiadherence factor preventing bacteria from adhering to the bladder wall would explain both the need for and the efficiency of the urine washout factor, Cox, C. E. and F. Hinman, Jr. (1961), "Experiments with induced bacteriuria, vesical emptying and bacterial growth on the mechanism of bladder defense to infection", J. Urol. 86:739-748. Human immonoglobulin A and glycoproteins have been studied as possible antiadherence factors acting in an antibody-like fashion, inactivating bacterial adherence mechanisms such as pili or the glycocalyx, Williams, R. C. and R. J. Gibbons (1972), "Inhibition of bacterial adherence by secretory immunoglobulin A: a mechanism of antigen disposal, "Science 177:697-699; Williams, R. C. and Gibbons, R. J.(1975), "Inhibition of streptococcal attachment to receptors on human buccal epithelia cells by antigenically similar salivary glycoproteins," Infect. Immuno. 11: 711-718. Such a mechanism would be less effective in the urinary bladder than at other mucous surfaces because it would require specific antibody production, which in turn requires prior exposure to antigens. Such a model does not adequately serve to explain the bladder's resistance to infection in the presence of a variety of environmental microorganisms.

Earlier investigations have shown that there is an interaction of microorganisms with mucosal surfaces as a prelude to infection on the surface of the bladder. Research efforts have shown that the ability of a bacterium to adhere to a mucous membrane is proportional to its virulence in the genitourinary tract, the gastrointestinal tract, and the oral cavity, Ellen, R. P. and R. J. Gibbons (1972), "M protein-associated adherence of *Streptococcus pyogenes* to epithelial surfaces: prerequisite for virulence", Infect. Immuno. 5:826-830; Gibbons, R. J., and J. van Houte (1971), "Selective bacterial adherence to oral epithelial surfaces and its role as an ecological determinant", Infect. Immun. 3:567-573; Punsalang, A. P., Jr., and W. D. Sawyer (1973), "Role of pili in the virulence of *Neisseria gonorrhoeae*", Infect. Immuno. 8:255-263; Sobelavsky, O., B. Prescott, and R. M. Chanock (1968), "Adsorption of *Mycoplasma pneumoniae* to neuraminic acid receptors of various cells and possible role in virulence", J. Bacteriol. 96:695-705; Svanborg-Eden, C., B. Eriksson and L. A. Hanson (1977), "Adhesion of *Escherichia coli*" to human uroepithelial cells in vitro", Infect Immun. 18:767-774; Swanson, Jr. 1973), "Studies on gonococcus infection. IV. Pili: their role in attachment of gonococci to tissue culture cells", J. Exp. Med. 137:571-589. It appears that the host has immunodefenses or "antiadherence factors" directed against this bacterial virulence factor. The operation of such a factor at the surface of the transitioral epithelium in the urinary tract seems to explain the resistance of the bladder to infection.

I have previously developed an in vivo model to quantitatively measure bacterial adherence to the urinary bladder, Parsons, C. L., C. Greenspan, and S. G. Mulholland (1975), "The primary antibacterial defense mechanism of the bladder", Invest. Urol. 13:72-76. Data obtained using the model suggest that the transitional cells lining the bladder synthesize one or more glycosaminoglycans (GAGS) which appear to prevent bacterial adherence to the mucosal cells, Parsons, C. L., C. Greenspan, S. W. Moore, and S. G. Mulholland (1977), "Role of surface mucin in primary antibacterial defense of bladder", Urology 9:48–52. I call this substance, antiadherence factor.

My earlier experiments show that the layer of GAGs lining the bladder can be removed by acid treatment, with a corresponding rise in bacterial adherence, but that when heparin, an exogenous GAG is added to bladders rendered mucin deficient, bacterial adherence drops to control levels, Hanno, P. M., C. L. Parsons, S. H. Shrom, R. Fritz, and S. G. Mulholland (1978), "The protective effect of intravesical heparin in experimental bladder infection", J. Surg. Res. 25:324–329. Additional studies suggested that heparin coats the transitional cells at the bladder surface and acts as a barrier between the bacterium and the transitional cell, Parsons, C. L., S. G. Mulholland, and H. Anwar (1979) "Antibacterial activity of bladder surface mucin duplicated by exogeneous glycosaminoglycan (heparin)", Infect. Immun. 24:552–557.

One important consideration with regard to this latter finding was whether the anticoagulant effect of heparin was responsible for the antiadherence activity detected. I have now discovered that the antiadherence properties of an exogenous sulfonated semisynthetic analogue of heparin possessing far less anticoagulant activity than heparin has the capability of blocking bacterial adherence in vivo. Thus, it is now possible to control and prevent bladder infections by irrigation without exposure to unwanted anticoagulant activity.

I have also discovered that many disease states involve a decrease in the anti-adherence activity of the GAG layer, which I believe is the important interface between the transitional cells and all harmful substances in urine. Thus this invention is applicable even in cases where no bacteriological infection is involved. One such disease state may be interstitial cystitis, with urine as the pathogen and a defective GAG layer in the patient. Bladder tumors are another, whereby the GAG layer prevents carcinogens from adhering to the transitional cells and inducing a tumor (Parsons, C. L., Schmidt, J. D., and Pollen, J. J. (1982) "Successful treatment of interstitial cystitis with sodium pentosanpolysulfate", New Engl. J. Med., submitted for publication; Kaufman, J. E. and Parsons, C. L., (1982) "The effect of tryptophan metabolites and cyclamate on the bladder surface glycosaminoglycans: A mechanism for carcinogenesis", Cancer Res., submitted for publication; Bodenstab, W., Stauffer, C., Schmidt, J. D. and Parsons, C. L. (1982), "Protective effects of bladder surface glycosaminoglycans against carcinogenic agents", Poster Presentation Annual Meeting, American Urological Association, Kansas City, Mo., May 16–20, 1982.

SUMMARY OF THE INVENTION

Briefly, the present invention comprises the method of treating bladder infections, interstitial cystitis and tumors in mammals which comprises the irrigation of the internal bladder and associated surfaces with an irrigating solution containing an effective amount of sodium pentosanpolysulfate.

This invention also includes novel irrigating solutions for the bladder containing an effective amount of sodium pentosanpolysulfate.

The invention further comprehends the oral administration of large doses of sodium pentosanpolysulfate to treat interstitial cystitis.

It is an object of my invention to provide a novel method for controlling and preventing infections in the bladder surfaces of mammals.

It is a more particular object of this invention to provide a novel method of controlling and preventing such infections by the irrigation of the internal bladder surface with sodium pentosanpolysulfate.

It is a major object of this invention to provide an improved procedure for the control and prevention of bladder infections in humans.

It is also an object of this invention to provide novel irrigating solutions for the bladder.

Yet another object is the use of sodium pentosanpolysulfate in patients free of bacterial infections to treat and control interstitial cystitis and bladder tumors.

These and other objects and advantages of my invention will appear from the more detailed description which follows.

DESCRIPTION OF THE PREFERRED EMBODIMENTS

I have now discovered that bladders rendered mucin-deficient with acid can be protected from clinical infection if they are pretreated with sodium pentosanpolysulfate prior to adding bacteria (see Table I).

EXAMPLE 1

TABLE I

| PROTECTION FROM INFECTION IN RABBIT BLADDERS PRETREATED WITH SODIUM PENTOSANPOLYSULFATE | | | |
|---|---|---|---|
| Experimental Group | Growth (No. of rabbits) | No Growth (No. of rabbits) | Total (No. of rabbits) |
| Control | 7 | 24 | 31 |
| Acid-Treated | 15 | 14 | 29 |
| Sodium Pensosanpoly-sulfate-Pretreated | 9 | 18 | 27 |
| Total | 31 | 56 | 87 |

The data show the ability of sodium pentosanpolysulfate to prevent urinary tract infection in rabbits whose bladders were rendered mucin-deficient via acid treatment and then pretreated with sodium pentosanpolysulfate for 30 minutes before instillation of $10^5$ bacteria (sodium pentosanpolysulfate-pretreated rabbits). Rabbits in the control group received 1 ml of $10^5$ bacteria alone; the acid-treated group consisted of rabbits whose bladders were rendered mucin-deficient via acid treatment before 1 ml of $10^5$ bacteria were added. The rabbits were checked for infection at 48 hours by collection of a catheterized urine specimen for culture; infection was considered to be present if any bacteria grew. The infection rate was significantly higher in acid-treated bladders than in controls ($p<0.02$) but there was no significant difference between infection rates in sodium pentosanpolysulfate pretreated bladders and infection rates in control bladders.

Materials and Methods

Rabbits—New Zealand white male rabbits weighing 4–6 lbs. were used for the experiment.

Bacteria—*E. coli* type 04 was employed for the studies. They were inoculated into trypticase soy broth in a 2½% (V/V) amount and incubated overnight for use the next day. They were sedimented at 3,000 X g for 10 minutes and resuspended in 0.9% saline (PSS) and washed once. The suspension of bacteria was diluted with PSS to a titer of $10^5$ colony forming units/ml and 1.0 ml of this solution was inoculated into rabbits via a #5 polyethylene tube.

Bacterial studies were done using trypticase soy agar. All rabbits were tested for bladder infection by plating 0.01 ml urine. Urine samples taken 48 hours after introduction of bacteria were also taken via catheter and cultured in the same fashion. Again any growth of bacteria was called positive (see Table I).

Introduction of bacteria into the rabbits: One ml of the bacterial suspension (as noted above) containing $10^5$ CFU/ml was placed via catheter into three groups of rabbits after their urine was cultured.

Group one—controls—bladders were rinsed with three 15.0 ml aliquots of phosphate buffered PSS and bacteria were given.

Group two—rabbits had their bladders rendered mucin-deficient by placing 0.4 normal HCl into their bladders for 2 minutes. The acid was removed and the bladder rinsed with three 15.0 ml aliquots of phosphate buffered saline. The bacteria were then introduced.

Group three—These bladders were also rendered mucin-deficient as above but 20.0 mg of sodium pentosanpolysulfate suspended in 1.0 ml of $H_2O$ was placed into the bladders for 30 minutes. It was then removed and 1.0 ml of $10^5$ CFU/ml of bacteria (also containing sodium pentosanpolysulfate) was added to the bladder.

Cultures—The rabbits were cultured prior to treating and at 48 hours.

Statistics—All data were subjected to a statistical analysis employing the student t test and are reported as significant if $P<0.05$.

Results—The results are summarized in Table I and as can be seen sodium pentosanpolysulfate treated rabbits had an infection rate not statistically different from control ($P>0.05$) while the acid treated rabbits had an infection rate significantly different from the controls ($P<0.02$).

EXAMPLE 2

Materials and Methods

Preparation of bacteria. *Escherichia coli* type 04 was labeled with $^{14}C$. After labeling, the bacteria were concentrated 10-fold and suspended in 0.1M sodium phosphate buffer (pH 5.5). This buffered solution was employed throughout the experiments.

Basic model of in vivo adherence assay.

Step 1. Male New Zealand White rabbits weighing 2 to 3 kg were used. All animals were anesthetized with pentobarbital, 18 mg/ kg of body weight. Each rabbit was secured and given 100 ml of physiological saline solution intravenously over a 30-min period. A pediatric feeding tube no. 8 French (C. R. Bard, Murray Hill, N.J.) was inserted into the urethra and secured with a 4-0 silk pursestring suture tied around the penis. The abdomen was opened to expose the bladder, permitting visual confirmation that the bladder was totally empty before each instillation. Between treatments the bladder was returned to the abdomen, and the overlying fascia were secured.

Step 2. (1) Control bladders: these were flushed with four 15-ml volumes of physiological saline solution. (ii) Acid-treated bladders: the mucin layer was removed by acid as previously described, Parsons, C. L., and S. G. Mulholland (1978), "Bladder surface mucin: its antibacterial effect against various bacterial species", Am. J. Pathol. 93:423-432, except that 0.6N HCl rather than 0.3 HCl was used. Throughout the experiments, all bladders were emptied of urine before any instillations.

Step 3. The bladders of control rabbits received 0.5 ml of buffered solution, followed immediately by 0.4 ml of bacteria suspended in buffer, and the catheter was clamped. The acid-treated bladders of test control rabbits (mucin layer absent) also received 0.5 ml of buffered solution, followed by 0.4 ml of bacteria (Step 1), and the catheter was clamped.

Sodium pentosanpolysulfate (supplied under the designation SP54 by Benechemie, Munich, Germany) was added to buffered saline in concentrations of either 40, 20, 10, 5, 2.5, 1, or 0.5 mg/ml. To each acid-treated bladder, under direct vision, was added 0.5 ml of this suspension, followed immediately with 0.4 ml of labeled bacteria suspended in buffer, and the catheter was clamped.

Before the addition of bacteria (Step 3), acid-treated bladders were treated with 1.0 ml of buffered solution containing 20 mg of sodium pentosanpolysulfate per ml for 30 min. This solution was removed by aspiration, and the bladder was washed twice with 15.0-ml volumes of buffered solution. The labeled bacteria (0.4 ml) were then added to the empty bladder, and the catheter was clamped.

Step 4. After the bacteria were introduced into the bladder, the catheter was clamped for 15 min. while saline was given intravenously at a rate of 200 ml/h. At the end of 15 min., 10 ml of buffer was introduced into the bladder to dilute the bacteria and terminate the reaction. The penile catheter was left to straight drainage, and, after the rabbit had made 50 to 70 ml of urine, the rabbit was sacrificed, and the bladder was removed. The mucosa was dissected free from the muscle layer, and both mucosal and muscle tissue were assayed for $^{14}C$ activity.

Step 5. Bladder tissue was placed in an incubator at 65° C. until desiccated, and a dry weight was determined. The mucosal tissue or muscle tissue was dissolved and bleached in a combination of 1.0 ml of 70% perchloric acid and 0.4 ml of 30% hydrogen peroxide. After 30 min., 2 or 3 drops of 15% ascorbic acid was added to remove the remaining hydrogen peroxide. The mocosal samples, muscle samples, and bacteria were suspended in Aquasol (New England Nuclear Corp., Boston, Mass.). Radioactive counts were recorded by a Searle liquid scintillation counter. Each sample was counted for 10 min.

All data were subjected to variance analysis using Student's t test. Differences in mean bacterial adherence values are reported as significant when $P<0.05$ and not significant when $P>0.05$.

The bacterial solution injected into the rabbits ranged between $1.0\times10^9$ and $2.0\times10^9$ colony-forming units per ml with a ratio of bacteria to counts per minute of between 300 and 500.

Results

Sodium pentosanpolysulfate and bacteria. The data are expressed in two ways: bacteria per milligram (dry weight) of mucosa, and the ratio of bacteria per milligram of mucosa for all groups for each given day of experimentation. This latter ratio is important because it has been noted that bacterial ability to adhere varies greatly from day to day, perhaps reflecting drifts in pili production, but that the ratio in adherence between experimental and control rabbits on any day is consistent. This ratio is presented in Table 2. In general, inter-experimental variability in adherence values were low. Over 95% of the time, the results obtained on a given day showed higher values for bacterial adherence to acid-treated bladders than to control bladders or to bladders receiving sodium pentosanpolysulfate.

As can be seen in Table 2, the sodium pentosanpolysulfate exerts its maximum effect at blocking adherence at concentrations of 5 to 10 mg/ml. For this reason, the bladders and bacteria were pretreated with sodium pentosansulfate at a concentration of 20 mg/ml, four times that needed to ensure an effect.

After acid treatment of the bladder mucosa, there was a rise in bacterial adherence to experimental rabbit bladders of an average of 50-fold, reflected in the ratio of bacteria bound per milligram of mucosa, between experimental and control rabbits. Bacterial adherence after acid treatment in experimental rabbits was significantly greater ($P<0.001$) than that in control rabbits. Adherence in the acid-treated bladders that received sodium pertosanpolysulfate in concentrations of 40, 20, 10 and 5 mg/ml was not significantly different from adherence in control bladders ($P>0.05$). Bacterial adherence in bladders at concentrations of sodium pentosanpolysulfate of 2.5, 1.0, and 0.5 mg/ml was significantly greater than adherence in control rabbits ($P<0.001$), but was not significantly different from that in the acid-treated controls (Table II). No bacteria were detected in the bladder muscle.

TABLE II

EFFECT OF SODIUM PENTOSANPOLYSULFATE ON BACTERIAL ADHERENCE IN BLADDERS RENDERED MUCIN DEFICIENT

| Mucosal group | $10^3$ mean bacteria per mg of mucosa ± $SD^a$ | N | Ratio, acid-treated bladders/controls[b] |
|---|---|---|---|
| Control[c] | 1.9 ± 1.7 | 25 | 1.0 |
| Acid[d] | 56 ± 69 | 20 | 49 ± 71 |
| Sodium pentasanpolysulfate[d] (concn, mg/ml): | | | |
| 40 | 2.4 ± 3.8 | 16 | 3.3 ± 6.0 |
| 20 | 5.0 ± 10 | 16 | 5.4 ± 7.2 |
| 10 | 2.5 ± 3.9 | 16 | 3.8 ± 4.9 |
| 5 | 7.6 ± 6.0 | 15 | 4.1 ± 3.9 |
| 2.5 | 9.8 ± 13 | 14 | 25.5 ± 43 |
| 1.0 | 25 ± 39 | 15 | 22.4 ± 41 |
| 0.5 | 22 ± 23 | 15 | 50 ± 93 |

[a]SD, Standard deviation.
[b]Ratio of acid-treated bladders to controls (± standard deviation) on each separate day of experimentation. This ratio is slightly higher than that obtained comparing overall mean ratio of adherence, since day-to-day variation of bacterial adherence has more effect on the overall means (see text).
[c]Bladder mucin present; no acid treatment.
[d]Baldder mucin absent, pretreated with acid.

As shown in Table III, pretreatment of bacteria with 20 mg of sodium pentosanpolysulfate per ml did not interfere with bacterial adherence in acid-treated bladders. A 54-fold increase in bacterial adherence to experimental bladders was seen when the ratio of bacteria adherent per milligram of mucosa of experimental bladders was compared to the ratio for control bladders on each day of experimentation. No statistically significant difference was found between adherence in the acid-treated bladder and adherence in the group of bladders that received bacteria pretreated with sodium pentosanpolysulfate.

The data presented in Table III indicate that pretreatment of the bladder with sodium pentosanpolysulfate partially blocked bacterial adherence to the experimental bladder. Adherence values demonstrated only a 9-fold rise, compared to the 55-fold rise in adherence seen in the acid-treated bladders without sodium pentosanpolysulfate. Statistically, these values were not significantly different from those for the control group of bladders.

TABLE III

EFFECT OF SODIUM PENTOSANPOLYSULFATE ON BACTERIAL ADHERENCE WHEN EITHER THE BACTERIA OR THE BLADDER IS PRETREATED WITH THIS COMPOUND

| Mucosal group | Mean bacteria per mg of mucosa ± $SD^a$ | N |
|---|---|---|
| Control[b] | 2.6 ± 3.3 | 16 |
| Acid[c] | 47.6 ± 78 | 20 |
| Bacteria pretreated with sodium pentosanpolysulfate[c] | 57.4 ± 92 | 15 |
| Bladder pretreated with sodium pentosanpolysulfate[c] | 9.4 ± 11.7[d] | 16 |

[a]SD, Standard deviation.
[b]Bladder mucin present; no acid treatment.
[c]Bladder mucin absent; pretreated with acid.
[d]This difference does not attain statistical significance when compared to controls ($P > 0.1$).

As a result of these findings there is enormous potential for such a use of this compound in clinical urology. Following a cystoscopic procedure, this compound can be instilled into the bladder and help prevent clinical infection. For this reason it is to be expected that the use of sodium pentosanpolysulfate intraluminally in bladders to prevent or reduce clinical urinary tract infection will be widely adopted.

TUMOR STUDY

It has been shown in animal models that the bladder surface is lined by a layer of glycosaminoglycans (GAGs) that prevents bacterial adherence and infection. The GAG layer also prevents calcium and proteins from adhering to the bladder surface. I believe the GAG layer acts as a nonspecific barrier between the transitional cells and the environment, protecting them from infection, stone formation, and carcinogenesis. To determine whether the GAG layer also blocks the access of carcinogens to the transitional cells, I tested the tumorigenic effects of n-methyl-n-nitrosourea (NMU), a complete carcinogen, in 5 groups of rats using an in vivo assay. Group I received NMU only; Group II underwent removal of the natural GAG layer with HCl followed by treatment with NMU; Group III underwent HCl removal of the GAG layer and its replacement with the sodium pentosanpolysulfate followed by treatment with NMU; Group IV received sodium pentosanpolysulfate followed by NMU; and Group V received HCl treatment only. All rat bladders were assayed for tumors at 18, 22, 26, 30, 34, and 38 weeks. Group II showed the highest incidence of tumors, approximately 60%. Approximately 37.5% of Group I rats, 25% of Group III rats, 9.1% of Group IV rats and 0% of Group V rats developed tumors. The differences between tumor incidence in the groups receiving sodium pentosanpolysulfate before NMU (Groups III and IV) and the group receiving NMU after HCl removal of the natural GAG layer (Group II) were statistically significant ($p<0.05$), suggesting that sodium pentosanpolysulfate prevented the increased carcinogenic effects of NMU seen in bladders whose natural GAG layer had been removed. These data suggest that both the natural GAG layer and sodium pentosanpolysulfate provide a barrier between the transitional cell and its environment which not only is capable of preventing infection but which also can inhibit the carcinogenic effects of compounds that potentially are present in the urine.

METHODS

Five groups of pathogen-free Wistar rats, averaging 150 grams in weight and fed on standard lab rodent chow and water ad lib, were anesthetized with intraperitoneal pentobarbital, catheterized with a 3.5 F feeding tube, and given doses of reagents by bladder irrigation according to the following schedule:

| GROUP | ACID | SODIUM PENTO-SANPOLYSUL-FATE | NMU | NUMBER BIWEEKLY DOSES |
|---|---|---|---|---|
| IA |   |   | X | 2 |
| IB |   |   | X | 3 |
| IC |   |   | X | 4 |
| II | X |   | X | 3 |
| III | X | X | X | 3 |
| IV |   | X | X | 3 |
| V | X |   |   | 3 |

Acid treatment consisted of instillation of 0.8 cc of 0.06N 9 HCl for one minute, drainage, one wash with pH 9 phosphate buffer and a second wash with pH 6.8 phosphate buffer. Treatment with sodium pentosanpolysulfate consisted of instillation of 0.55 cc of 16 mg/cc sodium pentosanpolysulfate for 15 minutes, removal, and one wash with pH 6.8 phosphate buffer. Treatment with NMU consisted of instillation of 0.50 cc of 2.0 mg/cc NMU for 20 minutes removal, and one wash with pH 6.8 phosphate buffer. Treatments were thus given at weeks 0, 2, 4, and 6.

Rats in Groups I through IV were then surveyed every four weeks beginning at Week 18 by anesthetizing each animal and transilluminating the full bladder via a small laparotomy in the manner described by Veenema. When definite bladder tumors were discovered, the animals were sacrificed, the bladders harvested, and tumors examined grossly and histologically. All animals were sacrificed by Week 38. If questionable tumors were discovered during transillumination, the animal was followed until positive determination could be made.

CONCLUSION

Hicks has demonstrated a linear dose response between the percentage of bladder tumor formation and the dose of NMU instilled intravesically. I found essentially the same response in our positive control arm (Group IB), which showed increased incidence of tumors with cumulative doses. In addition, I found that there was a rise in tumor incidence when the mucin layer was stripped from the bladder. NMU treatment yielded 60% tumors in these rats. When this was compared to the group receiving the carcinogen alone, in which the incidence of tumor development was 37.5%, the difference approached statistical significance ($p<0.1$). More importantly, when the bladder was acid treated, pretreated with sodium pentosanpolysulfate and then exposed to the carcinogen, there was a 25% incidence of tumor formation. The difference between tumor incidence in this group and in the group treated with acid and NMU only approached statistical significance ($p<0.07$). Lastly, when the bladder was pretreated with sodium pentosanpolysulfate and then exposed to NMU, only approximately 9% of the animals developed tumors. When the rate of tumor induction in this group was compared to that in Group II, the difference was statistically significant ($p<0.0$)

The data suggest that the bladder surface mucin offers significant protection against a complete carcinogen and that the synthetic, sodium pentosanpolysulfate, is more effective than the natural mucin at blocking the carcinogenic effects. I believe the bladder surface GAG is an important protective mechanism that may be the host's principal defense against the carcinogenic effects of urine or its constituents. These results complement my prior investigations, which showed that certain cocarcinogens or carcinogens (tryptophan metabolites and cyclamate) have the ability to inactivate the bladder surface GAG and reduce its ability to resist bacterial adherence. These observations support our prior concept that the bladder surface GAG is a non-specific anti-adherence factor which prevents many substances from interacting with the transitional cells. In such a non-specific manner the GAG prevents bacterial infections, renal calculus disease, and even carcinogenesis, making it a very effective defense mechanism. Further, the current data suggest that the drug of this invention may be even more effective than the natural GAG at protecting the transitional epithelium, offering a new potential modality for protecting high-risk individuals from the carcinogenic effects of urine.

INTERSTITIAL CYSTITIS STUDY

Clinical trials were conducted on human subjects suffering from bladder inflammation due to interstitial cystitis. Interstitial cystitis has been a disease state for which no cause or effective therapy has been developed. It is characterized by severe urinary urgency, frequency, nocturia and abdominal and perineal pain. Individuals affected with more advanced disease are often "bladder cripples" requiring major surgery in order to function. Less severe disease may leave the person functional but always significantly disabled.

Sodium pentosanpolysulfate has been used experimentally in low dosages (100 mg or less per day) by oral administration by others in an attempt to control or alter the blood clotting rate and related matters. These results have not been confirmed. The present study differs in that much larger dosages of over 100 mg per day and, preferably 150, 200, 250 or more mg. per day are used by the oral route. The higher dosages have been found to give a new result, viz, effectiveness in the treatment of interstitial cystitis.

Subjects

To enter the study all patients had to be treatment failures of dimethylsulfoxide therapy, hydrodilatation of the bladder, or both. Symptoms had to be present a minimum of three years and had to include either nocturia five times or greater or severe perineal or abdominal pain that was constant in nature or was associated with bladder filling or emptying. Patients needed to have symptoms with negative urine cultures. Due to persistence and severity of symptoms and failure to respond to standard therapy, all patients acted as their own historical controls.

Studies

All patients in the study first received a CBC, PT, PTT, cystoscopy and bladder biopsy, urine cytologies, urine analysis and culture, both standard and tubular.

Therapy

Patients were placed on sodium pentosanpolysulfate either 50 mg four times a day or 150 mg twice a day. The drug was administered orally.

Follow-up

Responses were evaluated at four weeks and at two month intervals thereafter. Follow-up cystoscopy was performed whenever the initial study revealed an acute ulcer present in the bladder. Patients were considered successfully treated if they had loss of 80% or more of their pain, diminished nocturia by more than one half, and 75% reduction in their urinary urgency.

Results

Fifteen patients have been treated from 6 to 18 months. All were females. Eighty percent of the patients had symptoms present for five or more years.

TABLE IV

| No. of patients | Duration of symptoms | Pain present | Nocturia 5-10 times | Response |
|---|---|---|---|---|
| 15 | >5 yrs - 80%<br>3-5 years - 20% | 100% | 100% | 14 (93%) |

One hundred percent of the patients had nocturia (greater than five times per night, average approximately eight times).

One hundred percent of patients had severe lower abdominal or perineal pain that was essentially constant or present daily.

Fourteen of the fifteen patients responded within 4-8 weeks with loss of pain and nocturia. Daytime frequency was least affected. Eighty percent of patients reported a decrease in daytime frequency but in their opinion voiding more frequently than "other people", voiding on the average of every 1-2 hours. All patients reported experiencing remarkable relief of pain and nocturia and improved lifestyle.

One subject failed to respond. She had had her symptoms for seventeen years, had a small capacity, fibrotic bladder and was being considered for urinary diversion or augmentation cystoplasty at the time she was placed on medication.

One patient had a chronic ulcer cystoscopically (present over two years) which was healed with three months of therapy.

Macroscopically, all the patients showed mild chronic inflammation on biopsy—none showed fibrosis. Two patients had recurrences of clinical symptoms but with an increased dose of SP54, remission was induced. Over a 15-month period one of those patients had two additional recurrences of symptoms that had lasted one to two weeks, were less severe, and resolved.

The results of these trials are summarized in the following table.

TABLE V

| Response to Sodium Pentosanpolysulfate | |
|---|---|
| Response | Number of pts. (%) |
| Improved | 14 (94%) |
| Failed | 1 (6%) |
| Relapsed* | 2 (13%) |

*Both patients had symptoms for several weeks and became asymptomatic. One patient had two more short recurrences associated with positive urine cultures and improved with therapy.

The foregoing data indicates the efficacy of sodium pentosanpolysulfate in patients that have confirmed interstitial cystitis.

This invention is applicable to mammals generally including humans.

It is to be understood that this invention is applicable to all of the well-known irrigation solutions presently available. The catherization procedures employed are also familiar to those skilled in the art.

Having fully described the invention, it is intended that it be limited only by the lawful scope of the appended claims.

I claim:

1. A method of treating bladder infections in mammals which comprises irrigating the internal bladder and associated surfaces with an irrigating solution containing an effective amount of sodium pentosanpolysulfate.

2. The method of claim 1 wherein the irrigating solution is saline.

3. The method of claim 1 wherein sodium pentosanpolysulfate is present in the irrigating solution in an amount of from about 1 to 20 mg/ml.

4. The method of claim 1 wherein sodium pentosanpolysulfate is present in the irrigating solution in an amount of from about 5 to 20 mg/ml.

5. A method of treating interstitial cystitis in mammals which comprises irrigating the internal bladder and associated surfaces with an irrigating solution containing an effective amount of sodium pentosanpolysulfate.

6. The method of claim 5 wherein the irrigating solution is saline.

7. The method of claim 5 wherein sodium pentosanpolysulfate is present in the irrigating solution in an amount of from about 1 to 20 mg/ml.

8. The method of claim 5 wherein sodium pentosanpolysulfate is present in the irrigating solution in an amount of from about 5 to 20 mg/ml.

9. A method of treating interstitial cystitis in a mammal which comprises orally administering an effective amount of sodium pentosanpolysulfate to the mammal in need of such treatment.

10. The method of claim 9 wherein at least about 100 mg of sodium pentosanpolysulfate is administered per day.

11. The method of claim 9 wherein about 150 to 300 mg of sodium pentosanpolysulfate is administered per day.

* * * * *